United States Patent [19]

Chandraratna

[11] Patent Number: 4,739,098
[45] Date of Patent: Apr. 19, 1988

[54] ETHYNYLPHENYL-CONTAINING RETINOIC ACID DERIVATIVES

[75] Inventor: Roshantha A. S. Chandraratna, El Toro, Calif.

[73] Assignee: Allergan, Inc., Irvine, Calif.

[21] Appl. No.: 910,096

[22] Filed: Sep. 22, 1986

[51] Int. Cl.[4] ............................................. C07C 69/76
[52] U.S. Cl. ...................................... 560/8; 562/405;
564/161; 568/308; 568/335; 568/743; 585/23;
560/103
[58] Field of Search .............. 560/8; 562/405; 585/23;
568/308, 335, 243; 564/161; 514/520, 544, 532

[56] References Cited

U.S. PATENT DOCUMENTS 4,532,343 7/1985 Dawson .................................. 560/8

OTHER PUBLICATIONS

Van Arendonk R. J. F. M. et al, Proc.-IUPAC Symp. Photochem., 7th, 343–346, Katholieke Univ. Leuv., Louvain, Belg.

Primary Examiner—Paul J. Killos
Attorney, Agent, or Firm—James M. Kanagy

[57] ABSTRACT

Retinoid-like activity is exhibited by compounds of the formula

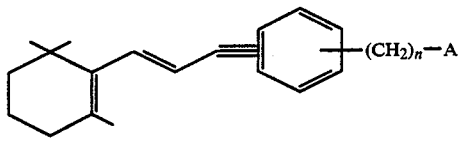

where n is 0–5 and A is H, lower alkyl, or —COOH or ester or amide thereof, —CH$_2$OH or an ether or ester derivative, or —CHO or an acetal derivative, or a pharmaceutically acceptable salt.

15 Claims, No Drawings

ETHYNYLPHENYL-CONTAINING RETINOIC ACID DERIVATIVES

BACKGROUND

This invention relates to novel compounds having retinoid-like activity. More specifically, the invention relates to compounds wherein three olefinic units from the acid-containing moiety in retinoic acid are replaced by an ethynylphenyl functionality. Such modifications to the retinoic acid structure have been found to retain retinoid acid-like activity.

RELATED ART

Nematocidal compounds disclosed in Japanese patent 56-123903, have the structure 2-(2-(((1,1-dimethyl)-dimethylsilyl)oxy)ethyl-alpha-(4-(2,6,6-trimethyl-1-cyclohexene-1-yl)-3-buten-1-ynyl)-1-cyclopentene-1-methanol which employs the 1-(2',6',6'-trimethyl-cyclohex-1'-enyl)-but-1-ene-3-yne moiety of the compounds disclosed herein. That fragment, however, is the only similarity between the Japanese compounds and those disclosed herein. Such compounds are not dispositive of the instant invention.

SUMMARY OF THE INVENTION

This invention covers compounds of formula I

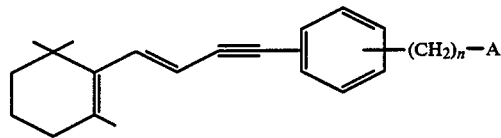

where n is 0–5 and A is H, lower alkyl, or —COOH or a pharmaceutically acceptable salt, ester or amide, —CH₂OH or an ether or ester derivative. or —CHO or an acetal derivative.

In a second aspect, this invention relates to the use of the compounds of formula I for treating dermatoses, such as acne, Darier's disease, psoriasis, icthyosis, eczema, atopic dermatitis and epithelial cancers. These compounds are also useful in the treatment of arthritic diseases and other immunological disorders (e.g., lupus erythematosus), in promoting wound healing and in treating the dry eye syndrome.

This invention also relates to a pharmaceutical formulation comprising a compound of formula I in admixture with a pharmaceutically acceptable excipient.

In another aspect, this invention relates to the process for making a compound of formula I where A is an acid or ester function, which process comprises reacting a compound of formula II with formula III in the presence of Pd(PQ₃)₄ (Q is phenyl) or a similar complex

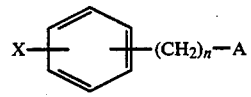

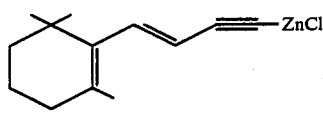

where n is 0–5 and A is H, lower alkyl, COOR, an ether or ester of —CH₂OH or an acetal derivative of —CHO, and X is Br or I when n=0, preferably I, or I when n is 1–5; or homologating a compound of the formula

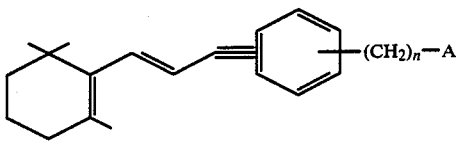

where
n is 0–4, and A is COOH, or
converting an acid of formula I to a salt; or
converting an acid of formula I to an ester; or
converting an acid of formula I to an amide; or
reducing an acid of formula I to an alcohol or aldehyde; or
converting an alcohol of formula I to an ether or ester; or
oxidizing an alcohol of formula I to an aldehyde; or
converting an aldehyde of formula I to an acetal.

GENERAL EMBODIMENTS

Definitions

The term "ester" as used here refers to and covers any compound falling within the definition of that term as classically used in organic chemistry. It includes organic and inorganic esters. Where A is —COOH, this term covers the products derived from treatment of this function with alcohols or thioalcohols. Where the ester is derived from compounds where A is —CH₂OH, this term covers compounds derived from organic acids capable of forming esters such as phosphorous-based and sulfur-based acids, or compounds of the formula —CH₂OCOR where R is any substituted or unsubstituted aliphatic, aromatic, heteroaromatic or aliphatic-aromatic group.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Here, and wherever else used, lower alkyl means having 1–6 carbon atoms. Also preferred are the phenyl or lower alkylphenyl esters.

Amides has the meaning classically accorded that term in organic chemistry. In this instance it includes the unsubstituted amides and all aliphatic and aromatic mono- and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and di-substituted amides derived from the substituted and unsubstituted phenyl or lower alkylphenyl amines. Unsubstituted amides are also preferred.

Acetals includes the radicals of the formula —CK where K is (—OR)₂. Here, R is lower alkyl. Also, K may be —OR₁O—where R₁ is lower alkylene of 2–5 carbon atoms, straight chain or branched.

A pharmaceutically acceptable salt may be prepared for any compounds in this invention having a functionality capable of forming such salt, for example an acid or an amine functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic acids or bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

The preferred compounds of this invention are those of formula I where the substituent is para to the ethynyl chain on the benzene ring; n is 0, 1 or 2; and A is —COOH, an alkali metal salt or organic amine salt, or a lower alkyl ester, or —CH$_2$OH and the lower alkyl esters thereof. The most preferred compounds are:

ethyl 4-[4'-(2", 6", 6"-trimethyl-cyclohex-1"-enyl)-but-3'-en-1'-ynyl]benzoate; and 4-[4'-(2", 6", 6"-trimethylcyclohex-1"-enyl)-but-3'-en-1'-ynyl]benzoic acid.

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pen. For topical application, these compounds could also be administered as a powder or spray, particularly in aerosol form.

If the drug is to be administered systemically, it may be confected as a powder, pill, tablet or the like, or as a syrup or elixir suitable for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intramuscular injection.

Other medicaments can be added to such topical formulation for such secondary purposes as treating skin dryness; providing protection against light; other medications for treating dermatosis; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in a prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for topical application. If administered systemically, an amount between 0.01 and 5 mg per kg per day of body weight would be expected to effect a therapeutic result in the treatment of many diseases for which these compounds are useful.

The retinoic acid like activity of these compounds was confirmed through the classic measure of retinoic acid activity involving the effects of retinoic acid on ornithine decarboxylase. The original work on the correlation between retinoic acid and decrease in cell proliferation was done by Verma & Boutwell, Cancer Research, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-0-tetradecanoylphorbol-13-acetate (TPA) induces ODC activity. Retinoic acid inhibits this induction of ODC activity by TPA. The compounds of this invention also inhibit TPA induction of ODC as demonstrated by an assay essentially following the procedure set out in Cancer Res.: 1662–1670, 1975.

SPECIFIC EMBODIMENTS

It is anticipated that the compounds of this invention can be made by a number of different synthetic chemical pathways. To illustrate this invention, there is here laid out a series of steps which have been proven to provide the compounds of formula 1 when such synthesis is followed in tone and in spirit. The synthetic chemist will readily appreciate that the conditions set out here are specific embodiments which can be generalized to any and all of the compounds represented by formula 1.

Compounds of formula 1 were prepared as follows:

Reaction Scheme I

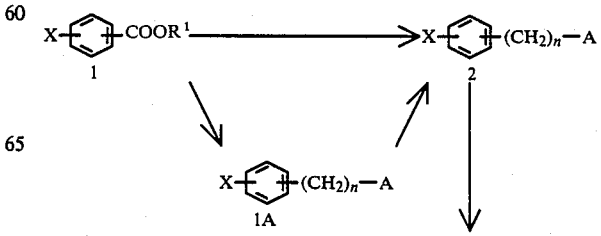

-continued
Reaction Scheme I

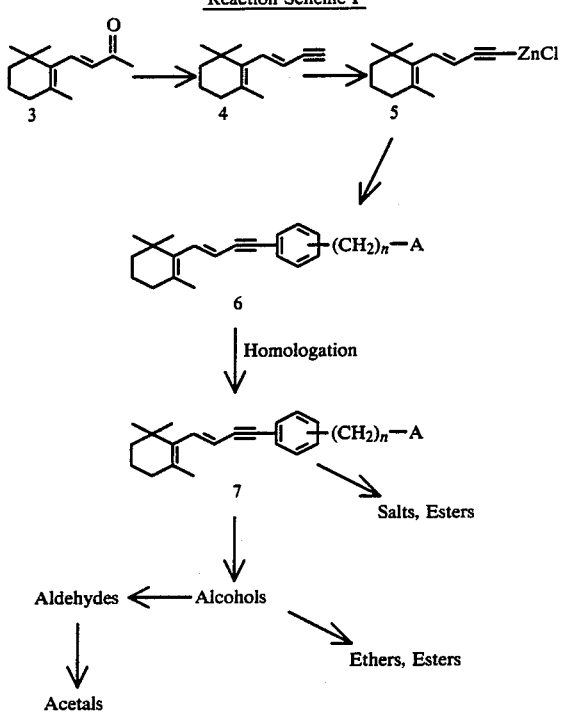

In the preceding reaction scheme, X is Br or 1 in formula 2 when n is 0 but preferably 1 and is 1 when n is 1-5. The radical R' is a lower alkyl radical in this reaction scheme.

The compounds of formula 2 are prepared from their corresponding acids. These acids (formula 1) are all available from chemical manufacturers or can be prepared by published methods. Esterification is effected by refluxing the acid in a solution of the appropriate alcohol in the presence of thionyl chloride. Refluxing for 2-5 hours provides the desired ester. The ester is recovered and purified by conventional means.

To obtain the compounds of formula 1A where n is 1-5, formula 1 compounds where R is hydrogen are subjected to homologation by successive treatment under Arndt-Eistert conditions. X in this case is I. These acids can then be converted to esters of formula 2 by the general procedure outlined in the preceding paragraph.

The compound of formula 3 is sold by Aldrich Chemical Company under the name Beta-Ionone. The acetylenic function is introduced by means of lithium diisopropylamide or a similar base at reduced temperature under an inert atmosphere. The reaction is carried out in an ether-type of solvent such as a dialkyl ether or a cyclic ether, for example, tetrahydrofuran, pyran or the like.

More specifically, lithium diisopropylamide is generated in situ by mixing diisopropylamine in a dry solvent such as tetrahydrofuran, which is then cooled, to between −70° and −50° C. under an inert atmosphere. An equimolar amount of an alkyllithium compound such as N-butyl lithium in an appropriate solvent is then added at the reduced temperature and mixed for an appropriate time to permit formation of lithium diisopropylamide (LDA). The ketone of formula 3 (at least a 10% molar excess) is dissolved in the reaction solvent. the solution cooled to that of the LDA mixture, and added to that solution. After brief mixing, the solution is then treated with a dialkyl chlorophosphate, preferably diethyl chlorophosphate in about a 20% molar excess. The reaction solution is then gradually brought to room temperature. This solution is then added to a second lithium diisopropylamide solution (about 2 equivalents) which is prepared in situ using dry solvent and under an inert atmosphere, preferably argon, at reduced temperature (e.g. −78° C.). Thereafter, the reaction mixture is again warmed to room temperature where it is stirred for an extended period of time, preferably between 10 and 20 hours, most preferably about 15 hours. The solution is then acidified and the product of formula 4 recovered by conventional means.

Formula 5 compounds are prepared under conditions which exclude water and oxygen. A dry, ether-type solvent such as dialkyl ether or a cyclic ether such as a furan or pyran, particularly a tetrahydrofuran, may be used as the solvent. A solution of formula 4 is first prepared under an inert atmosphere such as argon or nitrogen, and then a strong base such as N-butyl lithium is added (in about a 10% molar excess). This reaction is begun at a reduced temperature of between −10° and +10° C., preferably about 0° C. The reaction mixture is stirred for a short period, between 30 minutes and 2 hours, and then treated with about a 10% molar excess of fused zinc chloride dissolved in the reaction solvent. This mixture is stirred for an additional 1-3 hours at about the starting temperature, then the temperature is increased to about ambient temperature for 10-40 minutes.

To effect formation of formula 6, the alkyl halobenzoate, is dissolved in a dry reaction solvent. The ester is used in an amount approximating the molar quantity of the starting quantity of compound 4. This solution is introduced into a suspension of tetrakis-triphenylphosphine palladium (about a 5 to 10% molar amount relative to the reactants) in the reaction solvent at a temperature of between about −10° and +10° C. This mixture is stirred briefly, for about 15 minutes. To this just prepared mixture is then added the pre-prepared solution of formula 5, the addition being made at about room temperature. This solution is stirred for an extended period, between about 15 and 25 hours at room temperature. The reaction is then quenched with acid and the product separated and purified by conventional means to give the compounds of formula 6.

An alternative means for making compounds where n is 1-5 is to subject the compounds of formula 6 where n is 0 to homologation using the Arndt-Eistert method referred to above for the conversion of formula 1 compounds to formula 2 through homologation.

The acids, pharamaceutically acceptable salts and amides represented by formula 7 are readily obtainable from the esters of formula 6. Basic saponification with an alkali metal base will provide the acid. For example, an ester of Formula 6 may be dissolved in a polar solvent such as an alkanol, preferably under an inert atmosphere at room temperature with about a three molar access of base, for example, potassium hydroxide. The solution is stirred for an extended period of time, between 15 and 20 hours, cooled, acidified and the hydrolysate recovered by conventional means.

The amide may be formed by any appropriate amidation means known in the art. One way to prepare such compounds is to first make an acid chloride and then treat that compound with ammonium hydroxide or an appropriate amine. For example, the acid is treated with an alcoholic solution base such as ethanolic KOH (in approximately a 10% molar excess) and reacted at room temperature for about ½ hour. The solvent is removed and the residue taken up in an organic solvent such as ether, treated with a dialkyl formamide and then a 10-fold excess of oxalyl chloride. This is all effected at a reduced temperature between about −10° and +10° C. The last mentioned solution is then stirred at the reduced temperature for 1–4 hours, preferably 2 hours. Solvent removal provides a residue which is taken up in an inert inorganic solvent such as benzene, cooled to about 0° C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride (J. March, "Advanced Organic Chemistry". 2nd Edition, McGraw-Hill Book Company), then reducing the acid chloride with sodium borohydride (March, Ibid, pg. 1124), which gives the corresponding alcohols. Alkylating these alcohols with appropriate alkyl halides under Williamson reaction conditions (March, Ibid. pg. 357) gives the corresponding ethers.

Aldehydes can be prepared from the corresponding primary alcohols using mild oxidizing agents such as exemplified by pyridinium dichromate in methylene chloride (Corey, E. J., Schmidt, G., *Tet. Lett.*, 399, 1979).

Acetals can be prepared from the corresponding aldehyde by the method described in March, Ibid, p 810.

Compounds where A is hydrogen or lower alkyl are prepared from the corresponding iodphenyl entity. This iodophenyl compound is reacted with the ethynyl zinc chloride entity as described in Reaction Scheme I and more specifically in Example 3. Iodophenyl compounds where A is hydrogen or lower alkyl are commercially available or can be prepared by methods in the literature.

The following Examples are set out to illustrate the invention, not to limit its scope.

EXAMPLE 1

Ethyl 4-iodobenzoate

To a suspension of 10 g (40.32 mmol) 4-iodobenzoic acid (Alfa Products Thiokol/Ventron Division) in 100 ml absolute ethanol was added 2 ml thionyl chloride. This mixture was then heated at reflux for 3 hours. The solvent was removed in vacuo and the residue dissolved in 100ml of ether. The ether solution was washed with saturated NaHCO$_3$ and saturated NaCl solutions and dried (MgSO$_4$). Solvent was then removed in vacuo and the residue distilled on a kugelrohr apparatus (100° C.; 0.55 mm) to give 9 g of title compound as a colorless oil. PMR (CDCl$_3$)δ 1.42 (3H, t, J~7 Hz), 4.4 (2H, q, J~7 Hz), 7.8 (4H, s).

Proceeding in a similar manner, but substituting 2-iodobenzoic acid and 3-iodobenzoic acid, the following esters were made:

ethyl 3-iodobenzoate—PMR(CDCl$_3$)δ 1.4 (3H, t, J~7 Hz), 4.37 (2H, q, J~7 Hz), 7.12 (1H, t, J~8 Hz), 7.95 (2H, m), 8.37 (1H, s); and ethyl 2-iodobenzoate—PMR(CDCl$_3$)δ 1.4 (3H, t, J~8 Hz), 4.35 (2H, q, J~8 Hz), 7.25 (2H, m), 7.65 (2H, m).

This method can be used to make any esters needed for preparing the compounds claimed herein.

EXAMPLE 2

1-(2′, 6′, 6′-Trimethylcyclohex-1′-enyl)-but-1-ene-3-yne

A solution of 12.17 g (120.27 mmol) diisopropylamine in 200 ml dry tetrahydrofuran was cooled to −78° C. under argon and treated dropwise via syringe with 75 ml of 1.6M (120 mmol) n-butyllithium in hexane. This mixture was stirred at −78° C. for 1 hour and then treated via cannula with a cooled (−78° C.) solution of 21.99 g (114.35 mmol) β-ionone (Aldrich Chemical Company) in 20 ml of dry tetrahydrofuran. This mixture was stirred at −78° C. for 1 hour, treated dropwise with 21.73 g (125.93 mmol) of diethyl chlorophosphate and allowed to warm to room temperature over 2 hours. This mixture was then transferred by cannula to a solution of LDA prepared by stirring under Argon a solution of 26.57 g (262.57 mmol) of diisopropylamine in 150 ml dry tetrahydrofuran and 164 ml of 1.6M (262.4 mmol) n-butyllithium in hexane for 0.5 hour at −78° C. The mixture was allowed to warm to room temperature, stirred for 15 hours, acidified with 250 ml 3N HCl and extracted with pentane. The organic extract was washed with 1 N HCl, water, saturated NaHCO$_3$ and saturated NaCl and dried (MgSO$_4$). The product was concentrated and distilled on a kugelrohr apparatus (50° C; 0.1 mm Hg) to give the title compound as a colorless oil.

PMR (CDCl$_3$)δ 1.0 (2CH$_3$, s), 1.45 (2H,m), 1.65(CH$_3$,s), 1.92 (2H,m) 2.85 (1H,d,J~3 Hz), 5.35 (1H,dd, J~16 Hz, J~3 Hz), 6.6 (1H, d, J~16 Hz).

EXAMPLE 3

Ethyl 4-[4′-(2″, 6″, 6″-trimethylcyclohex-1″-enyl)-but-3′-en-1′-ynyl)benzoate

Reaction vessels used in this procedure were flame dried under vacuum and all operations were carried out in an oxygen-free argon or nitrogen atmosphere. To a solution of 970 mg (5.5656 mmol) of the acetylinic compound (formula 4) made in Example 2 in 5 ml dry tetrahydrofuran at 0° C. was added 3.6 ml of 1.6M (5.76 mmol) n-butyllithium in hexane. This mixture was stirred at 0° C. for 1.25 hour. The mixture was then treated via cannula with a solution of 790 mg (5.7968 mmol) fused zinc chloride in 4 ml dry tetrahydrofuran and stirred at 0° C. for 2 hours, then at room temperature for 20 minutes. A solution of 1.53 g (5.542 mmol) of ethyl 4-iodobenzoate in 4 ml dry tetrahydrofuran was transferred by cannula into a suspension of 450mg (0.3894 mmol) of tetrakis-triphenylphosphine palladium in 4ml dry tetrahydrofuran at 0° C. This mixture was stirred at 0° C. for 15 minutes. This mixture was then treated by cannula with the solution of the just prepared alkynyl zinc chloride compound and the resultant mixture was stirred at room temperature for 20 hours. The mixture was quenched by the addition of 30 ml 2N HCl and extracted with 100 ml of mixed hexanes and 100ml ether. Combined organic extracts were washed with saturated NaHCO$_3$ and NaCl solutions, dried (MgSO$_4$) and concentrated to give a brown oil. This oil was purified by medium pressure liquid chromatography (Waters 500; 2x silica prepak; 20% CH$_2$Cl$_2$ in hexanes) to give the title compound as a pale yellow oil. PMR (CDCl$_3$):δ 1.05 (2CH$_3$, s), 1.35 (3H, t, J~7 Hz), 1.5 (2H, m), 1.75 (CH$_3$, s), 2.0 (2H, M), 4.55 (2H, q, J~7 Hz), 5.65 (1H, d, J~16.5 Hz), 6.70 (1H, d, J~16.5 Hz), 7.4 (2H, d, J~8 Hz), 7.9 (2H, d, J~8 Hz).

Proceeding in a similar manner, but substituting the 2-iodo and 3-iodo analogs made in Example 1 for the ethyl 4-iodobenzoate, there were made the corresponding ortho and meta compounds whose PMR data are:

ethyl 3-[4'-(2",6",6"-trimethylcyclohex-1Cenyl)-but-3'-en-1'ynyl)benzoate—PMR(CDCl$_3$):δ 1.05 (2CH$_3$, s), 1.37 (3H, t, J~7 Hz), 1.50 (2H, m), 1.75 (CH$_3$, s), 2.0 (2H, m), 4.33 (2H, q, J~7 Hz), 5.65 (1H, d, J~16 Hz), 6.66 (1H, d, J~16 H ), 7.32 (1H, t, J~8 Hz), 7.55 (1H, dt, J~8, 1.6 Hz), 7.9 (1H, dt, J~8, 1.6 Hz), 8.07(1H, t, J 1.6 Hz): and.

ethyl 2-[4'-(2",6",6"-trimethylcyclohex-1"-enyl)-but-3'-en-1'-ynyl) benzoate—PMR(CDCl$_3$):δ 1.05(2CH$_3$, s), 1.42 (3H, t, J~7 Hz), 1.47 (1H, m), 1.60(1H, m), 1.78 (CH$_3$, s), 2.02 (2H, m), 4.4 (2H, q, J~7 Hz), 5.76 (1H, d, J~16 Hz), 6.73 (1H, d, J~16 Hz), 7.32 (1H, td, J~7, 1.5 Hz), 7.44 (1H, td, J~7, 1.5 Hz), 7.56 (1H, dd, J~7, 1.5 Hz), 7.94 (1H, dd, J~7, 1.5 Hz);

Proceeding in a similar manner, the following compounds may be made:
ethyl 4-[4'-(2",6",6"-trimethylcyclohex-1"-enyl)-but-3'-en-1'-ynyl]phenylacetate;
ethyl 3-[4'-(2",6",6"-trimethylcyclohex-1"-enyl)-but-3'-en-1'-ynyl]phenylacetate;
ethyl 2-[4'-(2",6",6"-trimethylcyclohex-1"-enyl)-but-3'-en-1'-ynyl]phenylacetate;
ethyl 3-(4-[4'-(2",6",6"-trimethylcyclohex-1"-enyl)-but-3'-en-1'-ynyl]phenyl)propionate;
ethyl 3-(2-[4'-(2",6",6"-trimethylcyclohex-1"-enyl)-but-3'-en-1'-ynyl]phenyl)propionate;
ethyl 3-(2-[4'-(2",6",6"-trimethylcyclohex-1"-enyl)-but-3'-en-1'-ynyl]phenyl)propionate;
ethyl 4-(4-[4'-(2",6",6"-trimethylcyclohex-1"-enyl)-but-3'-en-1'-ynyl]phenyl)butanoate;
ethyl 4-(3-[4'-(2",6",6"-trimethylcyclohex-1"-enyl)-but-3'-en-1'-ynyl]phenyl)butanoate;
ethyl 4-(2-[4'-(2",6",6"-trimethylcyclohex-1"-enyl)-but-3'-en-1'-ynyl]phenyl)butanoate;
ethyl 5-(4-[4'-(2",6",6"-trimethylcyclohex-1"-enyl)-but-3'-en-1'-ynyl]phenyl)pentanoate;
ethyl 5-(3-[4'-(2",6",6"-trimethylcyclohex-1"-enyl)-but-3'-en-1'-ynyl]phenyl)pentanoate; and
ethyl 5-(2-[4'-(2",6",6"-trimethylcyclohex-1"-enyl)-but-3'-en-1'-ynyl]phenyl)pentanoate.

EXAMPLE 4

4-[4'-(2",6",6"-trimethyl-cyclohex-1"-enyl)-but-3'-en-1'-ynyl]benzoic acid

To a solution of 292mg (0.9056 mmol) of ethyl 4-[4'-(2",6",6"-trimethylcyclohex-1"-enyl)-but-3'-en-1'-ynyl] benzoate in 1 ml ethanol under argon was added dropwise a solution of 180 mg (3.2 mmol) KOH in 2 ml ethanol and 0.5 ml water. This mixture was stirred at room temperature for 18 hours, cooled and acidified with 3N HCl. The resultant precipitate was dissolved in ether, the ether solution washed with saturated NaCl and concentrated to give a solid which recrystallized from methanol/water to give the title compound as a pale yellow solid. PMR (CDCl$_3$):δ 1.05 (2CH$_3$, S), 1.47 (1H, m), 1.62 (1H, m), 1.78 (CH$_3$, S), 2.05 (2H, m), 5.78 (1H, d, J~16 Hz), 6.78 (1H, d, J~16 Hz), 7.58 (2H, d, J~8 Hz), 8.02 (2H, d, J~8 Hz).

Proceeding in the same manner, but substituting for the benzoate above, a compound made as per Example 3, there may be made the following compounds:

3-[4'-(2",6",6"-trimethylcyclohex-1"-enyl)-but-3'-en-1'-ynyl]benzoic acid;
2-[4'-(2",6",6"-trimethylcyclohex-1"-enyl)-but-3'-en-1'-ynyl]benzoic acid;
4-[4'-(2",6",6"-trimethylcyclohex-1"-enyl)-but-3'-en-1'-ynyl]phenylacetic acid;
3-[4'-(2",6",6"-trimethylcyclohex-1"-enyl)-but-3'-en-1'-ynyl]phenylacetic acid;
2-[4'-(2",6",6"-trimethylcyclohex-1"-enyl)-but-3'-en-1'-ynyl]phenylacetic acid;
3-[-4'-(4'-(2",6",6"-trimethylcyclohex-1"-enyl)-but-3'-en-1'-ynyl)phenyl]propionic acid;
3-[-3-(4'-(2",6",6"-trimethylcyclohex-1"-enyl)-but-3'-en-1'-ynyl)phenyl]propionic acid;
3-[-2-(4'-(2",6",6"-trimethylcyclohex-1"-enyl)-but-3'-en-1'-ynyl)phenyl]propionic acid;
4-[-4'-(4'-(2",6",6"-trimethylcyclohex-1"-enyl)-but-3'-en-1'-ynyl)phenyl]butanoic acid;
4-[-3-(4'-(2",6",6"-trimethylcyclohex-1"-enyl)-but-3'-en-1'-ynyl)phenyl]butanoic acid;
4-[-2-(4'-(2",6",6"-trimethylcyclohex-1"-enyl)-but-3'-en-1'-ynyl)phenyl]butanoic acid;
5-[-4'-(4'-(2",6",6"-trimethylcyclohex-1"-enyl)-but-3'-en-1'-ynyl)phenyl]pentanoic acid;
5-[-3-(4'-(2",6",6"-trimethylcyclohex-1"-enyl)-but-3'-en-1'-ynyl)phenyl]pentanoic acid;
5-[-2-(4'-(2",6",6"-trimethylcyclohex-1"-enyl)-but-3'-en-1'-ynyl)phenyl]pentanoic acid;
6-[-4-(4'-(2",6",6"-trimethylcyclohex-1"-enyl)-but-3'-en-1'-ynyl)phenyl]hexanoic acid;
6[-3-(4'-(2",6",6"-trimethylcyclohex-1"-enyl)-but-3'-en-1'-ynyl)phenyl]hexanoic acid; and
6[-2-(4'-(2",6",6"-trimethylcyclohex-1"-enyl)-but-3'-en-1'-ynyl)phenyl]hexanoic acid.

EXAMPLE 5

4-[4'-(2",6",6"-Trimethylcyclohex-1"-enyl)-but-3'-en-1'-ynyl]benzamide

A mixture of 48.8 mg (0.1658 mmol) of EXAMPLE 4 and 1.3 ml of 0.14M (0.182 mmol) ethanolic KOH was stirred at room temperature for 0.5 hours and solvent removed in vacuo. The residue was dissolved in 2 ml ether, treated with 1 drop of dimethylformamide, cooled to 0° C. and then treated with 143 mg (1.1 mmol) of oxalychloride. After stirring at 0° C. for 2 hours, the mixture was filtered, the residue washed with ether and combined organic solutions concentrated. Residue was dissolved in benzene, cooled to 0° C. and treated dropwise with 1 ml of concentrated NH$_4$OH. The mixture was stirred at 0° C. for 2 hours, diluted with 25 ml water and extracted with ether. The ether extract was washed with saturated NaCl, dried (MgSO$_4$) and concentrated in vacuo to give the title compound as a white solid. PMR(CDCl$_3$): δ 1.05 (2CH$_3$, s), 1.46(1H, m), 1.6 (1H, m), 1.76(CH$_3$, s), 2.05 (2H, m), 5.7 (1H, d, J~16Hz), 6.27 (2H, broad s), 6.72 (1H, d, J~16 Hz), 7.5(2H, d, J~8 Hz), 7.76 (2H, d, J~8 Hz).

Proceeding in a similar manner, the compounds prepared as per Example 4 may be converted to their corresponding amide.

What is claimed is:
1. A compound of the formula

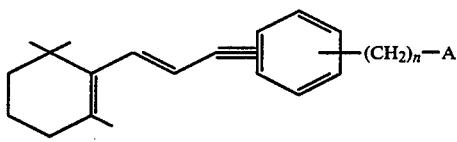

where n is 0–5 and A is H, lower alkyl, or —COOH or an ester or amide thereof: —CH₂OH or an ether or ester derivative: or —CHO or an acetal derivative: or a pharmaceutically acceptable salt.

2. A compound of claim 1 where n is 0.

3. A compound according to claim 2 where A is —COOH or an ester or amide, or a pharmaceutically acceptable salt thereof.

4. A compound according to claim 3 which is ethyl 4-[4'-(2",6",6"-trimethylcyclohex-1"-enyl)-but-3'-en-1'-ynyl]benzoate; or
4-[4'-(2",6",6"-trimethylcyclohex-1"-enyl)-but-3'-en-1'-ynyl]benzoic acid; or a pharmaceutically acceptable salt thereof.

5. A compound according to claim 2 where A is —CH₂OH or an ether or ester derivative, or a pharmaceutically acceptable salt thereof.

6. A compound according to claim 2 where A is —CHO or an acetal derivative thereof, or a pharmaceutically acceptable salt thereof.

7. A compound according to claim 1 wherein n is 1.

8. A compound according to claim 7 where A is —COOH or an ester or amide thereof, or a pharmaceutically acceptable salt thereof.

9. A compound according to claim 1 where n is 2.

10. A compound according to claim 9 where A is —COOH or an ester or amide thereof, or a pharmaceutically acceptale salt thereof.

11. A compound according to claim 1 where n is 3.

12. A compound according to claim 11 where A is —COOH or an ester or amide thereof, or a pharmaceutically acceptable salt thereof.

13. A method for treating psoriasis in a mammal which method comprises administering alone or in conjunction with a pharmaceutically acceptable excipient, a therapeutically effective amount of a compound of the formula

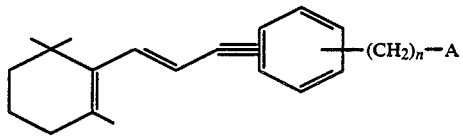

where n is 0–5 and A is H, lower alkyl, or —COOH or an ester or amide thereof; —CH₂OH or an ether or ester derivative; or —CHO or an acetal derivative; or a pharmaceutically acceptable salt.

14. A pharmaceutical composition comprising a pharmaceutically acceptable excipient and a compound of the formula

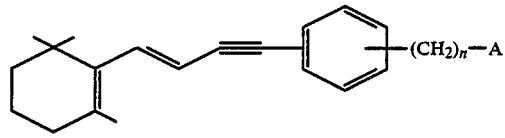

I where n is 0–5 and A is H, lower alkyl, or —COOH or an ester or amide thereof; —CH₂OH or an ether or ester derivative; or —CHO or an acetal derivative; or a pharmaceutically acceptable salt.

15. A compound according to claim 3 which is ethyl 3-[4'-(2",6",6"-trimethylcyclohex-1"-enyl)-but-3'-en-1'-ynyl]benzoate; or
3-[4'-(2",6",6"-trimethylcyclohex-1"-enyl)-but-3'-en-1'-ynyl]benzoic acid, or a pharmaceutically acceptable salt thereof.

* * * * *

UNITED STATES PATENT AND TRADEMARK OFFICE
CERTIFICATE OF CORRECTION

PATENT NO. : 4,739,098
DATED : April 19, 1988
INVENTOR(S) : Roshantha A. S. Chandraratna It is certified that error appears in the above-identified patent and that said Letters Patent is hereby corrected as shown below:

In the Abstract, lines 3 to 5, and Columns 11 and 12, Claims 1 and 13, the structual formula in each instances should appear as shown below.

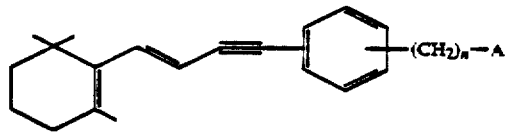

Signed and Sealed this

Twenty-seventh Day of September, 1988

Attest:

DONALD J. QUIGG

*Attesting Officer*          *Commissioner of Patents and Trademarks*